United States Patent [19]

Sandhaus

[11] Patent Number: 4,747,835

[45] Date of Patent: May 31, 1988

[54] SAFETY DEVICE FOR HYPODERMIC NEEDLES

[76] Inventor: Jeffrey Sandhaus, Box 253, Snedens Landing, Palisades, N.Y. 10964

[21] Appl. No.: 16,543

[22] Filed: Feb. 19, 1987

[51] Int. Cl.⁴ ............................................. A61M 5/32
[52] U.S. Cl. .................................... 604/192; 604/263
[58] Field of Search ........................ 604/192, 263, 187

[56] References Cited

U.S. PATENT DOCUMENTS 4,610,667 9/1986 Pedicano et al. ................... 604/192

FOREIGN PATENT DOCUMENTS 3433359 4/1986 Fed. Rep. of Germany ...... 604/263

Primary Examiner—John D. Yasko
Attorney, Agent, or Firm—Lerner, David, Littenberg, Krumholz & Mentlik

[57] ABSTRACT

A safety device for a hypodermic needle includes a hollow cylindrical portion, having an annular groove therein, disposed around the neck of a hypodermic syringe; a truncated conical surface disposed on the shoulder of the syringe; and a flexible projection abutting the neck. When a sheathed hypodermic needle engages the syringe, the safety device, via the groove therein, engages the sheath and is subsequently removed therewith. Upon recapping the needle, the conical surface shields the user from accidental puncture. Upon disengaging the sheathed needle from the syringe, the flexible projection closes behind the needle, retaining it in the sheath. Other embodiments of the invention include shields for precluding accidental needle puncture, and flexible projections for securing the needle in the sheath.

11 Claims, 5 Drawing Sheets

SAFETY DEVICE FOR HYPODERMIC NEEDLES

FIELD OF THE INVENTION

The present invention generally relates to medical devices. More particularly, the present invention relates to devices for use in connection with hypodermic needles and syringes. Still more particularly, the present invention relates to safety devices for preventing accidental puncture by hypodermic needles, and for safely retaining these needles in their sheaths.

BACKGROUND OF THE INVENTION

Accidental needle stick injuries continue to represent a significant percentage of the injuries which occur in the medical field. Such injuries generally occur when an individual such as a physician or nurse attempts to insert a hypodermic needle into its sheath after use. The opening in these conventional elongated needle sheaths is relatively small, and in maneuvering the needle for insertion thereinto, unless an extreme degree of care is employed, the point of the needle can miss the opening and puncture the fingers of the individual who is holding the sheath. Further injuries from hypodermic needles occur when housekeeping personnel in a hospital or other medical facility remove the used hypodermic needles from waste containers in order to dispose of them. In these waste containers, the needles may have separated from their sheaths, leaving them exposed, and accordingly, subjecting the housekeepers to accidental puncture therefrom.

Accidental puncture by a hypodermic needle therefore represents a common and serious risk to all medical personnel. According to an article in the "American Journal of Medicine" dated April, 1981, needle stick injuries accounted for one-third of all work-related accidents, with 60% of all such injuries occurring with nursing personnel. Such injuries pose a serious health hazard to the affected individual. According to this same article, accidental puncture by a hypodermic needle can engender serious disease, including potentially fatal viral hepatitis. Further, blood or other bodily fluids infected with the deadly AIDS virus may be introduced into such a puncture wound via contaminated needles. Accordingly, inadvertent needle sticks subject medical personnel to the risk of contracting highly contagious diseases, including potentially fatal viral hepatitis and acquired immune deficiency syndrome (AIDS).

Because of the serious nature of this problem, there have been many attempts to protect medical personnel from the risks of such needle punctures. These attempts have taken the form of a relatively large number of devices which are intended to be used instead of or in conjuction with the conventional syringes. One such prior art device for preventing inadvertent needle punctures entails a cylindrical plastic guard that slides up and covers the end of the needle after it has been used. Once the guard locks into place, it cannot be retracted. However, this safety device of the prior art entails several disadvantages. The cylindrical guard, which is disposed on the shaft of then needle, is a substantial portion of a length of the needle itself. Accordingly, a relatively small portion of the needle projects from the cylindrical guard. This renders the needle more difficult to manipulate and to position owing to the encumbrance of the guard on the shaft of the needle, and the obstruction of the view of the needle tip by the lengthy cylindrical guard. Further, hypodermic needles comprising such cylindrical guards are highly priced compared to conventional needles.

Pedicano et al, U.S. Pat. No. 4,610,667, discloses one form of known safety device. In this case, there is provided a disposable needle sheath which includes an elongated sleeve with a closed end and a funnel-shaped receiving guide at its open end. This device also includes a cap for sealing the open end after the needle has been inserted into the sleeve. In a preferred form of this device, as shown in FIGS. 6–12 thereof, means are provided within the sleeve 12 for grasping the needle hub therein. These can take the form of the needle locking threads 50 of FIGS. 6 and 7 and the gripping arms 58 of FIGS. 9 and 10. In each case, however, the needle remains accessible for removal from the open end of the sleeve. Furthermore, these devices are not usable with the conventional needle sheaths presently being utilized, but are intended to replace same.

There are also a large number of protective devices and packages which are intended to substantially encase a needle or a needle contained in a needle sheath. These include Hamilton, U.S. Pat. No. 3,021,442; Danish Pat. No. 133,797; German Pat. No. 1,240,228; Hamilton, U.S. Pat. No. 3,367,488; and Sampson, U.S. Pat. No. 4,425,120.

Mayer, U.S. Pat. No. 4,485,918, discloses apparatus for disposing of needles, including a funnel-like sheath 16 therein. The resheathed needle can then be disposed of in a container 40 having a slit aperture 43 for stripping the sheathed needle from the syringe spigot 20.

Additional patents include disclosures of protective sheaths which can be mounted on a syringe. For example, Nitshke, U.S. Pat. No. 4,232,669, discloses a sheath 16 having a separate cap 68 for maintaining on syringe 14 by functionally engaging syringe hub 26. Also, Brown, U.S. Pat. No. 3,677,247, discloses a syringe package 10 which includes a barrel cap 30 and a needle sheath 36. A frangible sheath is shown in Stevens, U.S. Pat. No. 3,073,307, and a separate sheath element is shown in Smith, U.S. Pat. No. 3,434,473.

Jagger et al, U.S. Pat. No. 4,592,744, discloses a self-resheathing needle assembly in which the syringe is removed from case 10 after use, and the needle assembly 30 is severed therefrom by contact with projections 52. Cooper, U.S. Pat. No. 4,629,453, discloses a protective cap 10 which includes a radially extending flange 2 to protect against misalignment of the needle, and Frist et al, U.S. Pat. No. 4,573,975, discloses a protective shield 14 which can be folded as in FIG. 3 thereof, and which is intended to protect the user's hand upon entry of the needle.

With all of these prior art devices, and in fact many more, none have been made available which can simply and easily be incorporated into conventional syringes and needle sheaths so as to effectively protect the users thereof. Furthermore, none of these devices can be mounted directly onto the forward end of a conventional syringe and also assist in the application of a conventional needle and needle sheath onto the syringe, insure proper needle application, and/or later act as a protective guard for the user when applying the used needle to the needle sheath.

Furthermore, none of these devices can be used to help insure that the needle itself is properly applied to the syringe. Finally, none of these prior art devices can be used to capture the needle hub therein so as to block extraction of the used needle from a needle sheath so as to facilitate disposal thereof.

SUMMARY OF THE INVENTION

In accordance with the present invention, these and other deficiencies of the prior art have been overcome by the invention of a safety device for use with a needle which comprises a tubular body portion, an enlarged annular shield projecting outwardly from the tubular body portion to provide a protective guard during insertion of a needle through the safety device, and occluding means for partially occluding the interior of the tubular body portion proximally of the proximal end of a needle when the needle is disposed within the safety device, in which the occluding means permits insertion of the needle into the tubular body portion from a first end thereof but blocks removal of the needle from the tubular body portion through that first end.

In accordance with one embodiment of the safety device of the present invention, the occluding means comprises an inwardly projecting flange, and most preferbly an inwardly projecting extension of the annular shield. In another embodiment the second end of the tubular body portion includes an elongated extension for accepting and enclosing the distal end of the needle therein.

In accordance with another embdiment of the safety device of the present invention which is intended to be used in connection with a needle sheath in which the needle is to be disposed, and in which the needle sheath includes an annular rim, the tubular body portion includes groove means at the second end of the tubular body portion for engaging the annular rim of the needle sheath upon insertion of the needle and the needle sheath into the second end of the tubular body portion.

In accordance with another embodiment of the safety device of the present invention, the device includes a tubular body portion including a first end and a second end, mounting means for mounting the first end of the tubular body portion on the forward portion of a syringe, an engagement means for engaging the safety device to the needle sheath upon mounting of the needle on the forward portion of the syringe so that the safety device will be removed from the syringe and needle upon removal of the needle sheath from the needle.

In accordance with this embodiment of the safety device of the present invention, there is also provided an enlarged annular shield projecting outwardly from the tubular body portion to provide a protective guard during insertion of the needle through the safety device. Preferbly, the mounting means includes occluding means for partially occluding the interior of the tubular body portion proximally of the proximal end of a needle when the needle is disposed within the safety device, the occluding means permitting insertion of the needle into the tubular body portion from that first end but blocking removal of the needle from the tubular body portion through that first end. In a preferred embodiment the occluding means comprises an inwardly projecting flange, preferably comprising an inwardly projecting extension of the annular shield.

In accordance with another embodiment of this safety device, the proximal end of the needle sheath includes an annular rim and the engagement means comprises groove means at the second end of the tubular body portion for engaging the annular rim of the needle sheath upon insertion of the needle and needle sheath into the second end of the tubular body portion.

In accordance with this embodiment it is preferred that the engagement means be spaced from the mounting means a predetermined distance, whereby when the needle and the needle sheath are inserted into the syringe with the safety device mounted thereon, the annular rim of the needle sheath only enters the groove means upon the mounting of the needle on the forward portion of the syringe.

A safety device in accordance with one embodiment of the present invention comprises a hollow cylindrical portion which is open at both ends and which includes a surface extending outwardly from one end thereof. Preferably, the surface is a truncated conical surface. An annular groove is disposed on the inside of the cylindrical portion at the end opposite the conical surface. A flexible projection extends inwardly from the cylindrical portion at the juncture of the surface and the cylindrical portion. This safety device can thus be disposed on the end of a conventional hypodermic syringe, with the conical surface situated on the shoulder of the syringe, the cylindrical portion surrounding the neck and outlet of the syringe, and the projection abutting the neck of the syringe. A hypodermic needle within a sheath can then be brought into engagement with the syringe by screwing the inlet of the needle into the neck of the syringe. In so doing, the groove at the end of the safety device engages the rim of the sheath. To utilize the needle and syringe, and the sheath, with the safety device hereof locked onto the rim thereof, are removed. After the needle has been employed, the combination of the sheath and the safety device is grasped behind the conical surface of the safety device, and the needle is inserted into the sheath. The conical surface functions as a shield to protect the user's hand from accidental puncture by the tip of the needle. To disengage the needle from the syringe, the sheath is twisted, unscrewing the needle from the neck of the syringe. The sheath, the needle, and the safety device coupled to the sheath, are then removed as a unit. In so doing, the projection on the safety device springs downwardly behind the end of the inlet of the needle, securing it within the sheath. The combination of the sheath, the needle therein, and the safety device are disposed of as a unit. Since separation of the needle from the sheath is prevented by the projection of the safety device, accidental punctures by the needle are precluded.

Another embodiment of the present invention entails a modified sheath for containing a hypodermic needle which includes a safety device permanently fixed to the end of the sheath surrounding the inlet of the needle. The safety device thus comprises an elongated sheath coupled to a first hollow cylindrical portion, and a larger, second hollow cylindrical portion coupled thereto. An enlarged annular surface extends outwardly from the end of the second cylindrical portion. Preferably, the surface is a truncated conical surface. A flexible projection extends inwardly from the second cylindrical portion, disposed behind the rim of the inlet of the needle. The needle is brought into engagement with a hypodermic syringe by twisting the sheath to screw the inlet of the needle into the neck of the syringe. In so doing, the conical surface of the safety device is disposed against the shoulder of the syringe, and the flexible projection abuts the neck of the syringe. To utilize the needle and the syringe, the combination of the sheath and the safety device thereon is removed from the needle. After the needle has been employed, the combination sheath and safety device is grasped behind the conical surface of the safety device, and the needle is inserted into the sheath. The conical surface functions as a shield, preventing accidental puncture of the user's hand. With the sheath and safety device fully applied to the needle so that the conical surface is disposed on the shoulder of the syringe, and the flexible projection abuts the neck thereof, the needle is disengaged by twisting the sheath to unscrew the inlet of the needle from the neck of the syringe. The sheath, the needle therein, and the safety device are then removed as a unit from the syringe. In so doing, the flexible projection springs downwardly behind the rim of the inlet of the syringe, securing the needle within the sheath. The combination of the sheath, the needle therein, and the safety device are discarded as a unit. Owing to the projection disposed behind the end of the needle, the needle is prevented from separating from the sheath. In this fashion, accidental punctures by the needle are prevented.

In another embodiment of the present invention, a safety device is slidingly coupled to the end of a conventional hypodermic needle sheath. The safety device thus comprises a hollow cylindrical portion spaced from the exterior of the sheath. An annular projection extends inwardly from one end of the cylindrical portion, in contact with the exterior surface of the sheath. A surface extends outwardly from the other end of the cylindrical portion. Preferably, the surface is a truncated conical surface. A flexible annular projection extends inwardly from the juncture of the cylindrical portion and the conical surface, disposed behind the rim of the sheath. To apply the combination of the sheath and the safety device slidingly coupled thereon to a needle and syringe, the combination is held behind the conical surface and the needle is inserted thereinto. The conical surface serves as a shield, preventing accidental puncture of the user's hand by the tip of the needle. When the combination has been applied to the needle such that the end of the sheath engages the inlet of the needle, the safety device is pushed towards the syringe until the conical surface is situated on the shoulder thereof. In so doing, the flexible projection disposed behind the rim of the sheath rides thereover, and abuts the neck of the syringe. The other projection moves behind the rim of the sheath. To disengage the needle from the syringe, the sheath is twisted to unscrew the inlet of the needle from the neck of the syringe. The combination of the sheath, the needle therein, and the safety device slidingly coupled to the sheath are removed as a unit from the syringe. In so doing, the flexible projection of the safety device moves from the neck of the syringe, flexing downwardly behind the inlet of the needle. In this fashion, the needle is securely retained within the sheath by this projection of the safety device. Since the needle cannot separate from the sheath, accidental punctures by the needle are thereby prevented.

The present invention permits hypodermic needles to be safely inserted into their sheaths without risk of accidental needle punctures. Also, by firmly retaining the needles within their sheaths, the present invention further prevents accidental punctures, particularly those occurring during disposal of the needles by housekeeping personnel. Owing to its simple design, the present invention may be readily and very inexpensively manufactured.

Accordingly, the present invention entails a facile, inexpensive, and efficacious means for eliminating extremely dangerous, accidental hypodermic needle punctures.

DETAILED DESCRIPTION OF THE PREFERRED EMBODIMENTS

Figure 1:
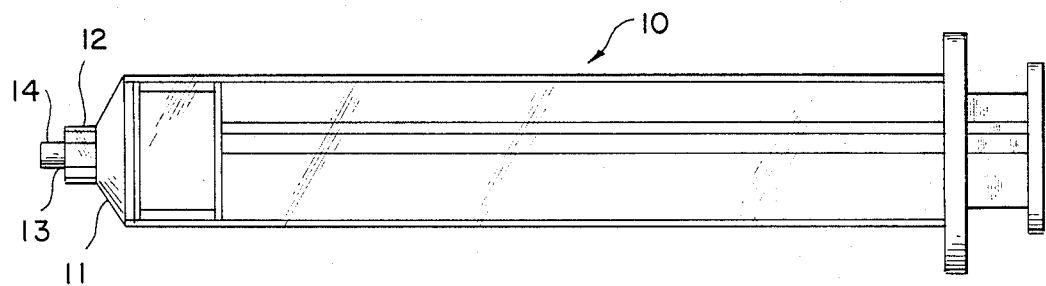
FIG. 1 is a side, elevational view of a conventional hypodermic syringe.

Referring to Figures in which like numerals refer to like portions thereof, FIG. 1 shows a conventional hypodermic syringe generally designated 10 including a neck 12 disposed on a shoulder 11 at the forward end thereof. Threads 13 are disposed on the interior surface of the neck 12, which is also referred to as a Luer tip mechanism. An outlet 14, having an aperature therein, is disposed within the neck 12, and is firmly attached to the shoulder 11 of the syringe 10.

Figure 2:
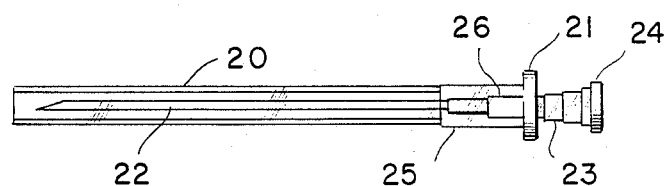
FIG. 2 is a side, elevational view of a conventional hypodermic needle sheath, and a conventional hypodermic needle inserted thereinto.

Referring to FIG. 2, a conventional hypodermic needle 22 is shown therein, including a hollow inlet or hub 23 for frictionally surrounding and engaging the outlet 14 of the syringe 10. A rim 24 is disposed on the end of the hub 23. A needle sheath 20 is designed to hold the hypodermic needle 22. The interior surface of the proximal end portion 25 of the sheath 20 is generally grooved to engage projections 26 on the hub 23, so as to prevent relative rotation of the needle 22 and the sheath 20 when the needle 22 is fully inserted into the sheath 20. A rim 21 is disposed on the end of the sheath 20.

Figure 4:
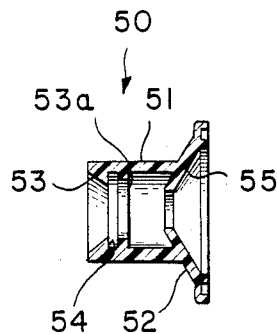
FIG. 4 is a side, sectional view of a safety device in accordance with the present invention.
Figure 5:
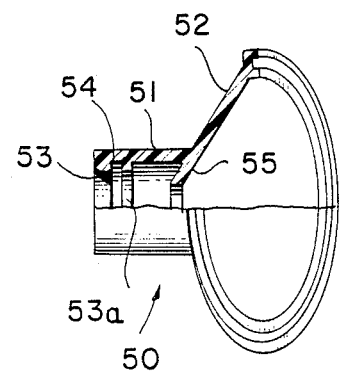
FIG. 5 is a side, perspective view, partially in section, of the safety device in accordance with the present invention as shown in FIG. 4.

Referring to FIGS. 4 and 5, a safety device 50 for a hypodermic needle in accordance with one embodiment of the present invention is depicted. The safety device 50 includes a hollow tubular section 51 which in this case is cylindrical, and which includes a surface 52 extending outwardly therefrom. Preferably, surface 52 comprises a truncated conical surface, which comprises the enlarged annular shield of this invention. A bevelled surface 53 is disposed on the end of the safety device 50 opposite the surface 52. A groove 54 is disposed adjacent the bevelled surface 53, and is defined between an inner annular wall member 53a and the bevelled surface 53. Preferably, both the bevelled surface 53 and the groove 54 are annular. An occluding means such as a flexible projection or projections 55 extends inwardly from the end of the cylindrical portion 51. Preferably, the projection 55 is inclined towards the end of the device 50 containing the groove 54. The occluding means or projection 55 is preferably a continuous annulus, but may comprise a plurality of discrete segments.

Figure 3:
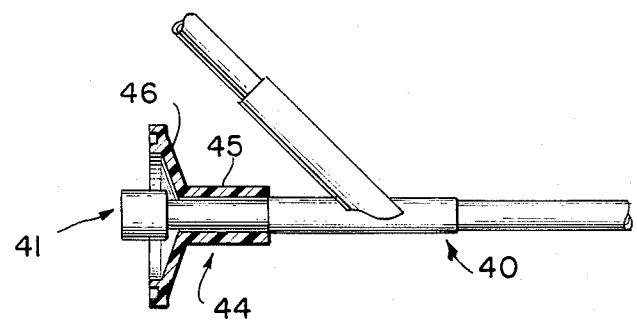
FIG. 3 is a partial, side, elevational view of conventional intravenous tubing having a side port for insertion of a hypodermic needle thereinto, and a sectional view of a safety device disposed on the side port, in accordance with the present invention.

Referring next to FIG. 3, intravenous tubing 40 having a side port 41, also known as a Y-connection, is depicted. A safety device 44, similar to that depicted in FIG. 3, includes a hollow cylindrical portion 45 disposed on the exterior surface of the intravenous tubing 40, and a surface 46 extending outwardly from the tubing 40. Preferably, the surface 46 comprises a truncated conical surface. The safety device 44 is preferably disposed proximate the end of the side port 41. To insert a hypodermic needle into the side port 41, the safety device 44 is held behind the surface 46 so that should the needle miss the aperature of the side port 41, the user's fingers are shielded therefrom by the surface 46. The safety device 44 may be permanently affixed to the intravenous tubing 40 at the side port 41, or detachably coupled thereto.

Figure 6:
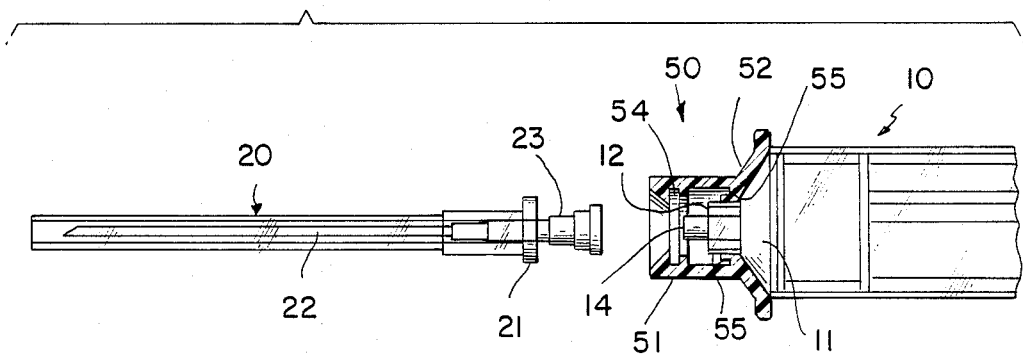
FIG. 6 is a side, elevational, exploded, partially sectional view of a conventional hypodermic syringe, in conjunction with a safety device in accordance with the present invention, and a conventional hypodermic needle sheath.

Referring to FIG. 6, the safety device 50 of FIGS. 4 and 5 is disposed on the shoulder 11 of hypodermic syringe 10. The occluding means 55 of the safety device 50 abuts the exterior of the neck 12 of the syringe 10. In this fashion, the safety device 50 is secured on the end of the syringe 10. The cylindrical portion 51 of the safety device 50 surrounds and extends beyond the neck 12 and the inlet 14 of the syringe 10. Owing to the conformity of the device 50 with the syringe 10, the device 50 and the syringe 10 may thus be easily packaged as a unit.

Figure 7:
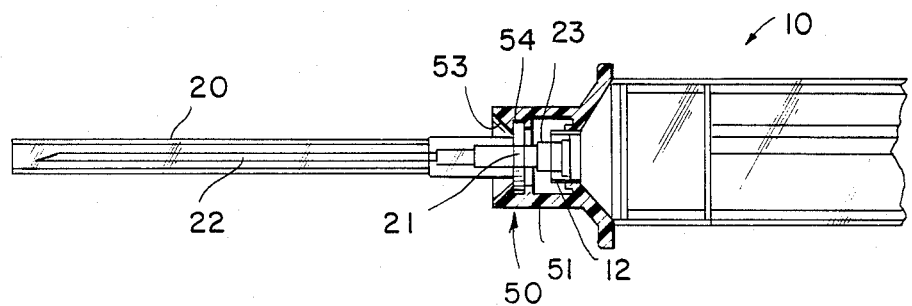
FIG. 7 is a side, elevational, partially sectional view of the device shown in FIG. 6 in which the needle is brought into engagement with the syringe, and the safety device is locked onto the rim of the sheath.

Referring to FIG. 7, with continuing reference to FIG. 6, the hypodermic needle 22 is next brought into engagement with the syringe 10 by moving the sheath 20 with the needle 22 therein towards the forward end of the syringe 10. The inlet 23 of the needle 22 is then fit into the neck 12 of the syringe 10 with the outlet 14 disposed within the inlet 23. The sheath 20 is rotated, thereby screwing the inlet 23 into the neck 12 of the syringe 10. As the needle 22 is brought into engagement with the syringe 10, the rim 21 of the sheath 20 contacts the bevelled surface 53 of the safety device 50, forcing the surface 53 outwardly. As the rim 21 continues to move forward, the cylindrical portion 51 resiliently closes, engaging the rim 21 in the groove 54. In this fashion, as the needle 22 is brought into engagement with the syringe 10, the safety device 50 is securely affixed to the rim 21 of the sheath 20. Furthermore, if the distance between the groove 54 and the shoulder 11 of the syringe 10 is appropriately selected, then the rim 21 will not enter the groove 54 until the needle 22 has been securely and perfectly mated with the syringe 10. This device thus helps assure that the needle is properly and securely affixed to the syringe, since if this is not the case, the needle 22 will remain within the needle sheath 20 when it is subsequently withdrawn.

Figure 8:
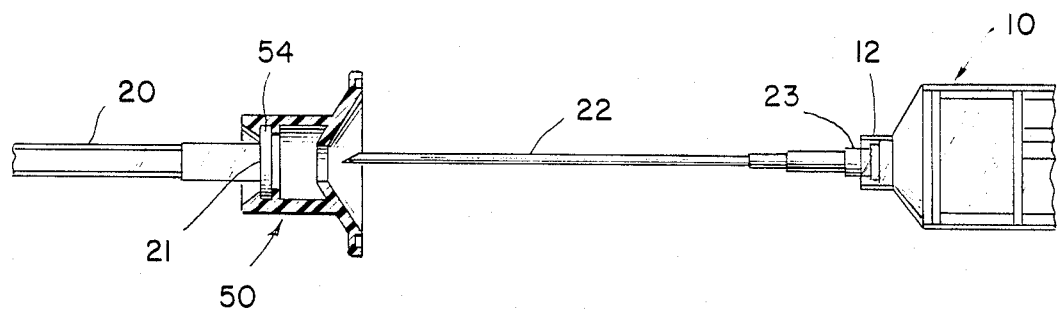
FIG. 8 is a side, elevational, partially sectional view of the device shown in FIG. 7 in which the sheath with the safety device locked thereon is removed from the combination of the hypodermic syringe and needle.

Referring to FIG. 8, after the needle 22 has been properly and fully screwed into the neck 12 of the syringe 10, the sheath 20 is withdrawn from the needle 22. In so doing, the safety device 50, which is locked onto the rim 21 of the sheath 20, is removed from the syringe 10. The needle is now ready for use.

Figure 9:
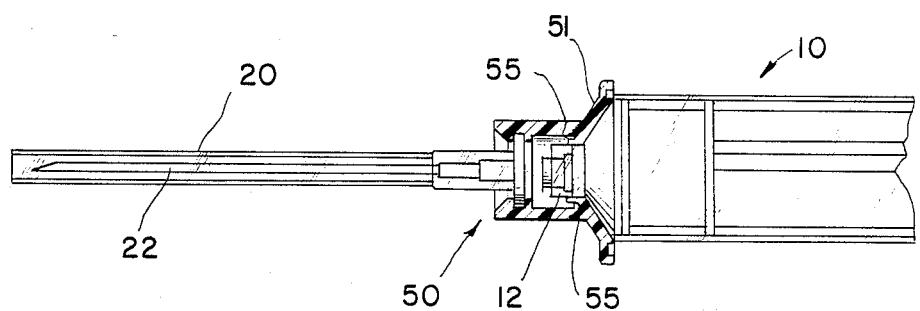
FIG. 9 is a side, elevational, partially sectional view of the device shown in FIG. 8 in which the sheath with the safety device locked thereon is applied to the combination of the hypodermic syringe and needle.

Referring next to FIG. 9, after the needle 22 has been employed, the needle 22 is inserted into the safety device 50 and the sheath 20. In so doing, the sheath 20 is held behind the safety device 50 so that the surface 52 shields the user's hand from accidental puncture by the tip of the needle 22. The needle 22 is inserted into the sheath 20 so that the flexible projection 55 of the safety device 50 abuts the neck 12 of the syringe 10. The used needle 22 has now been safely and easily secured in the needle sheath 20.

Figure 10:
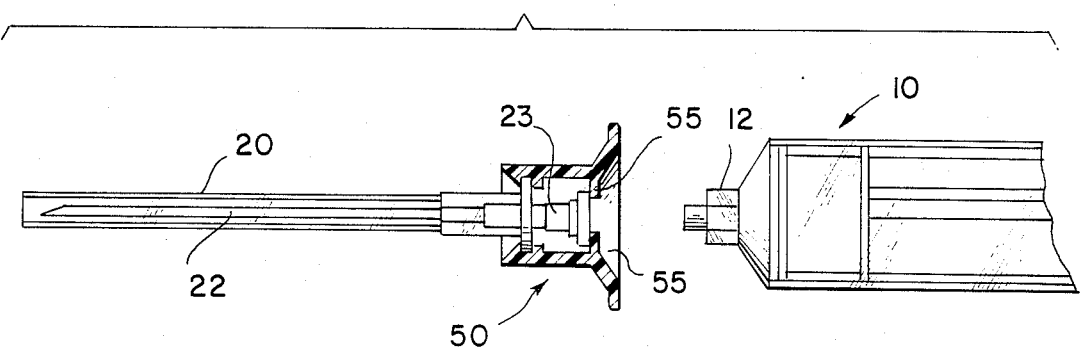
FIG. 10 is a side, elevational, partially sectional view of the device shown in FIG. 9 in which the sheath, the needle, and the safety device are disengaged from the hypodermic syringe, with the safety device retaining the needle within the sheath.

Referring next to FIG. 10, to then dispose of the used needle 22, the sheath 20 is twisted to unscrew the inlet 23 from the neck 12 of the syringe 10. In withdrawing the sheath 20 with the needle 22 therein and the safety device 50 from the syringe 10, the flexible projection 55 passes beyond the neck 12 and closes behind the inlet 23 and the rim 24, so as to partially occlude the interior of the tubular body 51, and to block the end of the needle therein. In this fashion, the needle 22 is securely retained within the sheath 20 and cannot be removed from the end of the needle sheath 20. The combination of the sheath 20, the safety device 50, and the needle 22 may now be discarded as a unit. Since the needle 22 is fixed within the sheath 20, it cannot separate from the sheath 20 to engender accidental punctures.

A particular advantage of the safety device 50 shown in FIGS. 4-10 is that it constitutes an integral unit which is separate and apart from the needle sheath 20 itself. Thus, as compared to the many prior art devices which include an elongated needle sheath or the like as part of the device itself, such as the Pedicano et al U.S. Pat. No. 4,610,667, the safety device 50 can easily be distinguishable from the needle sheath, such as by being produced in a different color or the like. This, in turn, further assists in permitting identification of the device during replacement of the used needle into the device and the needle sheath, such as by assisting in directing the user's eye focus, etc.

Figure 11:
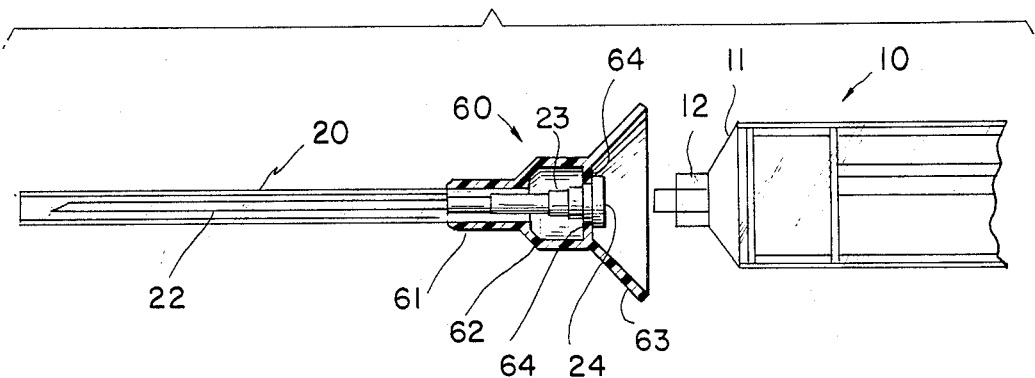
FIG. 11 is a side, elevational, partially sectional view of a conventional hypodermic syringe, hypodermic needle and sheath, with the needle inserted in the sheath and disengaged from the syringe, and a safety device according to the present invention, coupled to the end of the sheath.

Referring next to FIG. 11, another embodiment of the present invention is depicted. In this case, a safety device 60 is disposed at the end of and as an integral unit within needle sheath 20. The safety device 60 in this case thus includes a first hollow tubular or cylindrical portion 61 extending from the end of an elongated sheath 20. A second larger hollow cylindrical portion 62 then extends from the front hollow cylindrical portion 61. A surface 63 then extends outwardly from the second cylindrical portion 62. Preferably, the surface 63 comprises a truncated conical surface. A flexible projection or projections 64 extend inwardly from the end of the second cylindrical portion 62, initially being disposed behind the rim 24 of the inlet 23 of the needle contained within the safety device 60. Preferably, the projection 64 is a continuous annulus, but may comprise a plurality of discrete segments.

Figure 12:
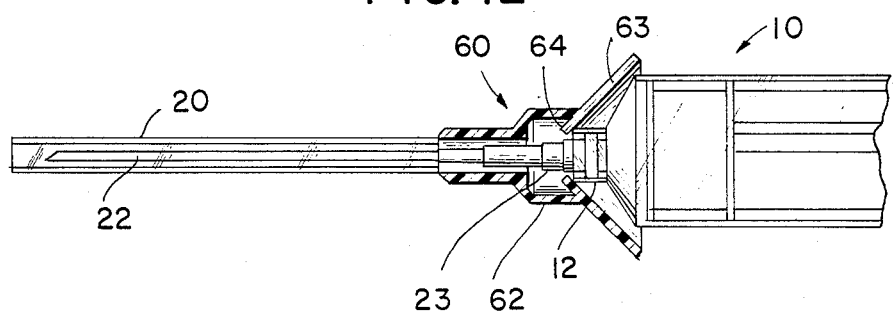
FIG. 12 is a side, elevational, partially sectional view of the device shown in FIG. 11 in which the hypodermic needle and the safety device are brought into initial contact with the hypodermic syringe.
Figure 13:
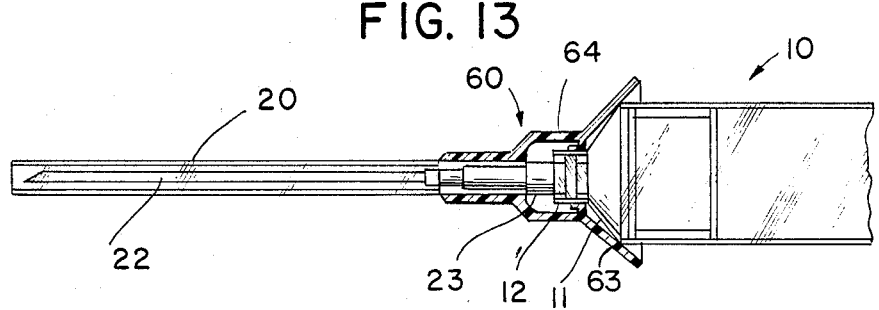
FIG. 13 is a side, elevational, partially sectional view of the device shown in FIG. 12 in which the hypodermic needle and safety device are brought into full engagement with the hypodermic syringe.

Referring next to FIG. 12, the needle 22 is brought into engagement with the syringe 10 by moving the sheath 20 towards the syringe 10 and twisting it to screw the rim 24 of the inlet 23 into the neck 12 of the syringe 10. In so doing, the flexible projection 64 is displaced inwardly and upwardly in the second cylindrical portion 62 of the safety device 60, and it is therefore now possible to easily remove the safety device 60 and employ the sterile needle 22.

Referring next to FIG. 12, when the inlet 23 has been fully screwed into the neck 12 of the syringe 10, the surface 63 abuts the shoulder 11 of the syringe 10, and the flexible projection 64 abuts the neck 12 thereof.

To utilize the needle 22, the sheath 20 with the safety device 60 is removed therefrom. After use of the needle, the safety device 60 can then be replaced over the used needle in much the same manner as is discussed above. That is, the enlarged annular shield 63 will act as a guard to protect the user's fingers from any accidental puncture from the used needle. FIG. 12 depicts the status of the needle 22 with the sheath 20 and the safety device 60 fully applied thereto.

Figure 14:
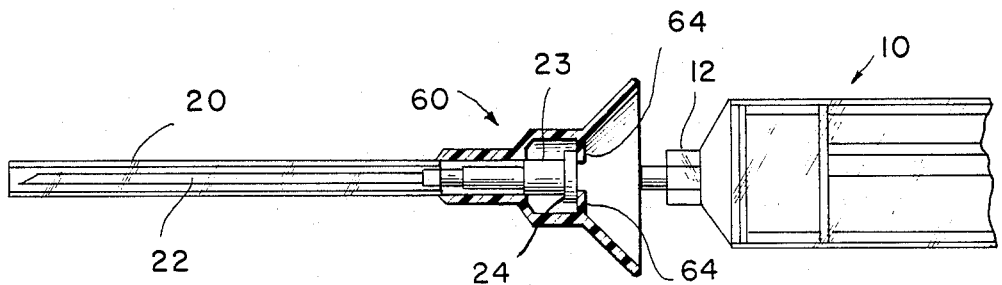
FIG. 14 is a side, elevational, partially sectional view of the device shown in FIG. 13 in which the hypodermic needle, the sheath, and the safety device are disengaged from the hypodermic syringe, with the safety device securely retaining the needle within the sheath.

Referring next to FIG. 14, to disengage the needle 22 from the syringe 10, the sheath 20 is twisted to unscrew the inlet 23 from the neck 12 of the syringe 10. The combination of the sheath 20 and the safety device 60 with the needle 22 therein are withdrawn from the syringe 10. In so doing, the flexible projection 64 passes along the outer surface of the neck 12 of the syringe 10, and springs downwardly behind the rim 24 of the inlet 23. Accordingly, the flexible projection 64 securely retains the needle 22 within the sheath 20. The combination of the sheath 20, the safety device 60, and the needle 22 therein can then be discarded as a unit. The projection 64 prevents the needle 22 from being dislodged from the sheath 20, thereby preventing accidental punctures by the needle 22.

Figure 15:
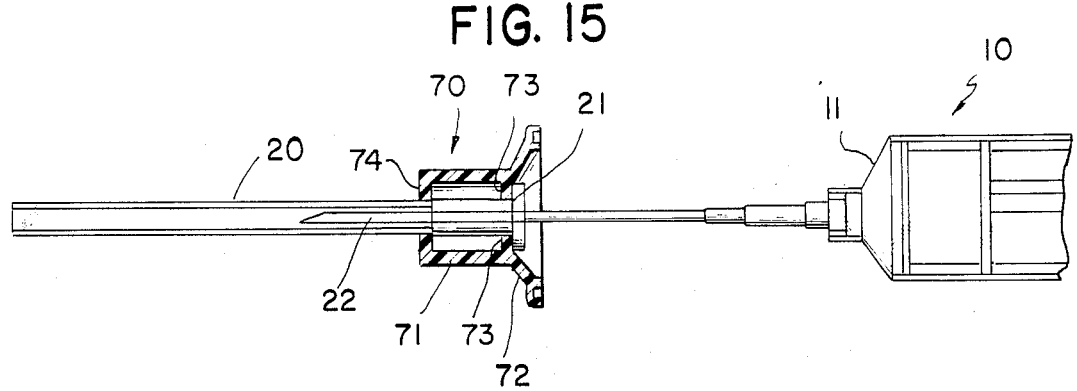
FIG. 15 is a side, elevational, partially sectional view of a conventional hypodermic needle, needle syringe, and needle sheath with the needle partially disposed therein, and a safety device according to the present invention, slidingly disposed on the end of the sheath.
Figure 16:
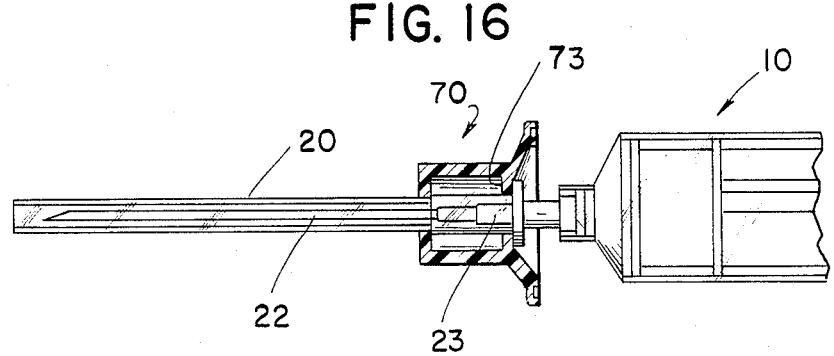
FIG. 16 is a side, elevational, partially sectional view of the device shown in FIG. 15 in which the sheath is fully applied to the hypodermic needle.

Referring next to FIG. 15, another embodiment of the safety device of the present invention is depicted. In this case, safety device 70 is slidingly disposed on a conventional needle sheath 20. The safety device 70 comprises a hollow cylindrical portion 71 spaced from the exterior surface of the sheath 20, and an inwardly projecting annular flange member 74 extending inwardly from the cylindrical portion 71, abutting the external surface of the sheath 20. The flange member 74 is preferably a continuous annulus, but may comprise a plurality of discrete segments. A surface 72 again comprising the enlarged annular shield hereof extends outwardly from the end of the cylindrical portion 71 of the device 70. Preferably, the surface 72 again comprises a truncated conical surface. A flexible projection 73 extends inwardly from the cylindrical portion 71, and is disposed behind the rim 21 of the sheath 20. The projection 73 is preferably a continuous annulus, but may comprise a plurality of discrete segments. Referring also to FIG. 16, after utilization of the needle 22, the combination of the sheath 20 and the safety device 70 coupled thereto is applied to the needle 22 by grasping the combination behind the surface 72, which functions as the protective shield hereof. In this fashion, upon insertion of the needle 22 into the safety device 70 and the sheath 20, accidental puncture is precluded.

Figure 17:
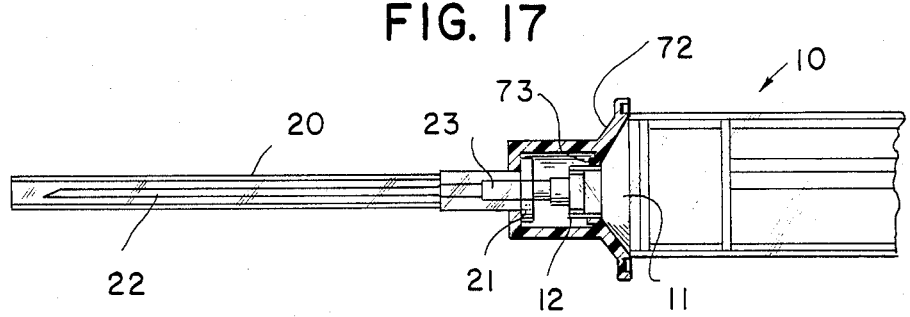
FIG. 17 is a side, elevational, partially sectional view of the device shown in FIG. 16 in which the safety device is moved forwardly on the sheath, in contact with the shoulder of the hypodermic syringe.

Referring to FIG. 17, with the end of the sheath 20 in engagement with the inlet 23 of the needle 22, the safety device 70 is pushed along the sheath 20 towards the syringe 10 until the surface 72 abuts the shoulder 11 of the syringe 10. In so doing, the flexible projection 73 moves over the rim 21 to abut the neck 12 of the syringe 10. Also, the member 74 abuts the rim 21 of the sheath 20.

Figure 18:
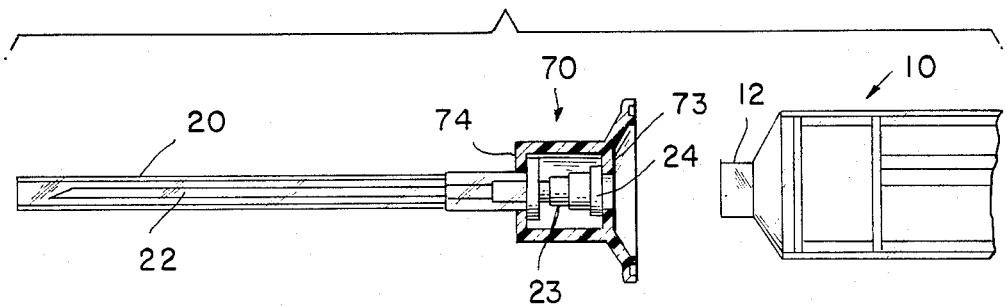
FIG. 18 is a side, elevational, partially sectional view of the device shown in FIG. 17 in which the hypodermic needle, sheath, and safety device are disengaged from the hypodermic syringe, with the safety device securely retaining the needle within the syringe.

Referring next to FIG. 18, to disengage the needle 22 from the syringe 10, the sheath 20 is twisted to unscrew the inlet 23 from the neck 12 of the syringe 10. The combination of the sheath 20, the safety device 70, and the needle 22 inserted therein are removed from the syringe 10. In so doing, the projection 73 passes off the neck 12 of the syringe 10, and resiliently springs behind the rim 24 of the inlet 23. In this fashion, the needle 22 is securely retained within the sheath 20. The combination of the sheath 20, the safety device 70, and the needle 22 therein are disposed of as a unit. Owing to the projection 73 which fixes the needle 22 in the sheath 20, the needle 22 may not separate from the sheath 20. In this fashion, danger of accidental puncture by the needle 22 is eliminated.

While the invention has been described in its preferred embodiments, it is to be understood that the words which have been used are words of description rather than limitation, and that changes within the purview of the appended claaims may be made without departing from the true scope and spirit of the invention in its broader aspects.

I claim:

1. A safety device for use with a needle including a distal end and a proximal end terminating in a needle rim, said safety device comprising a tubular body portion including a first end and a second end, an enlarged annular shield projecting outwardly from said tubular body portion so as to provide a protective guard during insertion of said needle through said safety device, and occluding means for partially occluding the interior of said tubular body portion proximally of said proximal end of said needle when said needle is disposed within said safety device, said occluding means comprising an inwardly projecting flange capable of cooperatively engaging said needle rim at said proximal end of said needle, said occluding means being located adjacent to said first end of said tubular body portion and having sufficient size and flexibility to be capable of permitting insertion of said needle into said tubular body portion from said first end and at the same time of cooperatively engaging the outer surface of said needle rim at said proximal end of said needle so as to block removal of said needle from said tubular body portion through said first end.

2. The safety device of claim 1 wherein said inwardly projecting flange comprises an inwardly projecting extension of said annular shield.

3. The safety device of claim 1 wherein said second end of said tubular body portion includes an elongated extension for accepting and enclosing said distal end of said needle therein.

4. The safety device of claim 1 intended to be used in connection with a needle sheath in which said needle is to be disposed including a distal end and a proximal end corresponding to said proximal end of said needle, said proximal end of said needle sheath including an annular rim, and wherein both said first and second ends of said tubular body portion comprise open ends and wherein said tubular body portion includes groove means at said second end of said tubular body portion for engaging said annular rim of said needle sheath upon the insertion of said needle and said needle sheath into said second end of said tubular body portion.

5. A safety device for use with a syringe including a forward portion, a needle including a distal end and a proximal end intended to be mounted on said forward portion of said syringe, and a needle sheath in which said needle is to be disposed including a distal end and a proximal end corresponding with said proximal end of said needle, said safety device comprising a tubular body portion including a first end and a second end, mounting means for mounting said first end of said tubular body portion on said forward portion of said syringe, and engagement means for engaging said safety device to said needle sheath upon said mounting of said needle on said forward portion of said syringe so that said safety device will be removed from said syringe and needle upon removal of said needle sheath from said needle.

6. The safety device of claim 5 including an enlarged annular shield projecting outwardly from said tubular body portion so as to provide a protective guard during isertion of said needle through said safety device.

7. The safety device of claim 6 wherein said mounting means includes occluding means for partially occluding the interior of said tubular body portion proximally of said proximal end of said needle when said needle is disposed within said safety device, said occluding means permitting insertion of said needle into said tubular body portion from said first end but blocking removal of said needle from said tubular body through said first end.

8. The safety device of claim 7 wherein said occluding means comprises an inwardly projecting flange.

9. The safety device of claim 8 wherein said inwardly projecting flange comprises an inwardly projecting extension of said annular shield.

10. The safety device of claim 5 wherein said proximal end of said needle sheath includes an annular rim, and wherein said engagement means comprises groove means at said second end of said tubular body portion for engaging said annular rim of said needle sheath upon the insertion of said needle and said needle sheath into said second end of said tubular body portion.

11. The safety device of claim 10 wherein said engagement means is spaced from said mounting means a predetermined distance, whereby when said needle and said needle sheath are inserted into said syringe with said safety device mounted thereon, said annular rim of said needle sheath only enters said groove means upon the mounting of said needle on said forward portion of said syringe.

* * * * *